United States Patent
Bauerle et al.

(10) Patent No.: US 7,143,787 B1
(45) Date of Patent: Dec. 5, 2006

(54) MICROLUIDIC VALVE HAVING TWO REVOLVING VALVE ELEMENTS

(75) Inventors: Martin Bauerle, Buhlertal (DE); Friedhelm Koch, Karlsbad (DE)

(73) Assignee: Agilent Technologies, Inc., Palo Alto, CA (US)

( * ) Notice: Subject to any disclaimer, the term of this patent is extended or adjusted under 35 U.S.C. 154(b) by 12 days.

(21) Appl. No.: 11/134,131

(22) Filed: May 20, 2005

(30) Foreign Application Priority Data

May 22, 2004 (EP) .................... 4102250

(51) Int. Cl.
*F16K 11/12* (2006.01)

(52) U.S. Cl. ............... 137/625.46; 137/637.5

(58) Field of Classification Search ........... 137/594, 137/625.46, 625.47, 637.5
See application file for complete search history.

(56) References Cited

U.S. PATENT DOCUMENTS

| | | | | |
|---|---|---|---|---|
| 3,700,003 A | * | 10/1972 | Smith | 137/614.17 |
| 4,187,872 A | * | 2/1980 | Freeman et al. | 137/454.6 |
| 4,444,066 A | * | 4/1984 | Ogle et al. | 73/863.72 |
| 5,270,212 A | * | 12/1993 | Horiuchi et al. | 436/45 |
| 5,616,300 A | | 4/1997 | Ford et al. | |
| 5,804,701 A | * | 9/1998 | Berger | 73/23.42 |
| 6,701,774 B1 | * | 3/2004 | Srinivasan et al. | 73/23.42 |
| 6,845,968 B1 | * | 1/2005 | Killeen et al. | 251/304 |
| 6,852,291 B1 | * | 2/2005 | Johnson et al. | 422/103 |
| 6,910,503 B1 | * | 6/2005 | Schick et al. | 137/625.47 |
| 2003/0015682 A1 | | 1/2003 | Killeen et al. | |
| 2003/0017609 A1 | * | 1/2003 | Yin et al. | 436/161 |
| 2003/0116206 A1 | | 6/2003 | Hartshorne et al. | |
| 2003/0224531 A1 | * | 12/2003 | Brennen et al. | 436/180 |

FOREIGN PATENT DOCUMENTS

| | | |
|---|---|---|
| EP | 1162464 | 12/2001 |
| WO | WO 01/84143 | 11/2001 |

* cited by examiner

*Primary Examiner*—John Fox

(57) ABSTRACT

A component part of a microfluidic valve adapted to be coupled with a microfluidic device, the microfluidic device having at least one port coupled to a flow path of the microfluidic device, the component part comprising a first revolving valve element having a first interface with the microfluidic device and a second revolving valve element having a second interface with the microfluidic device and being located within a through hole of the first revolving valve element.

10 Claims, 4 Drawing Sheets

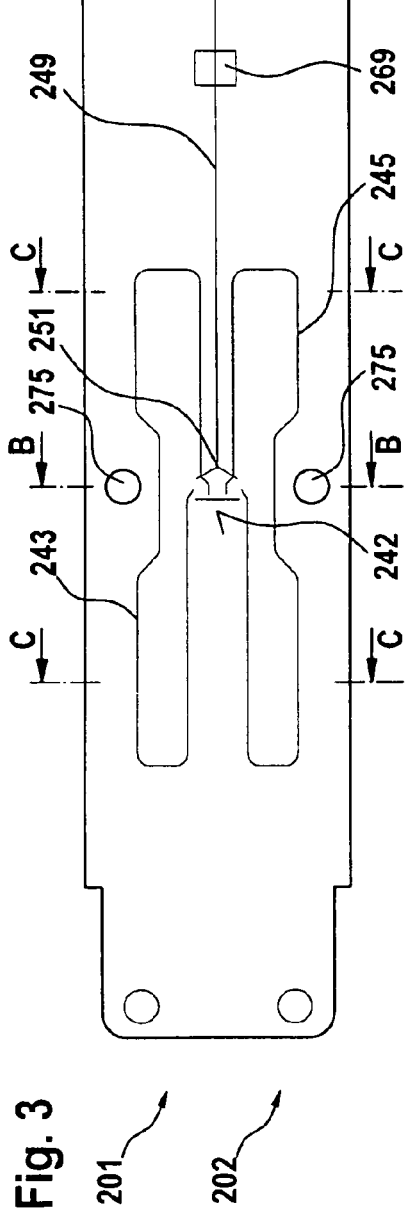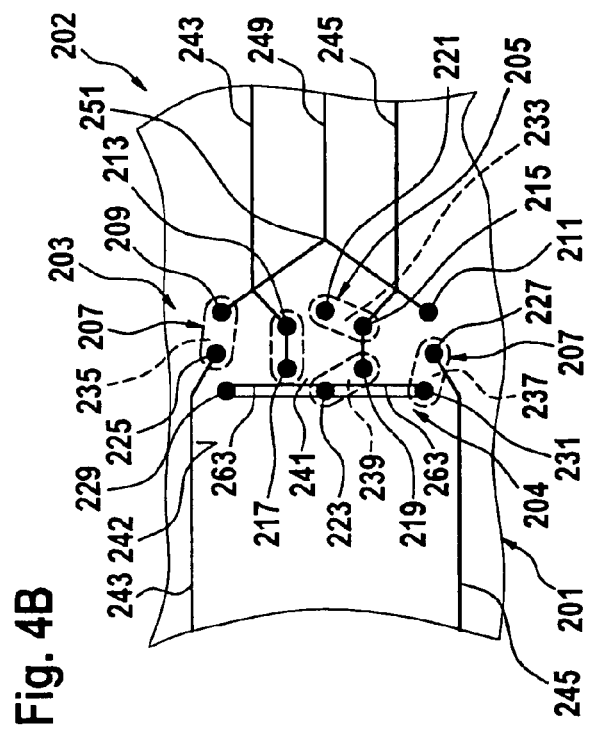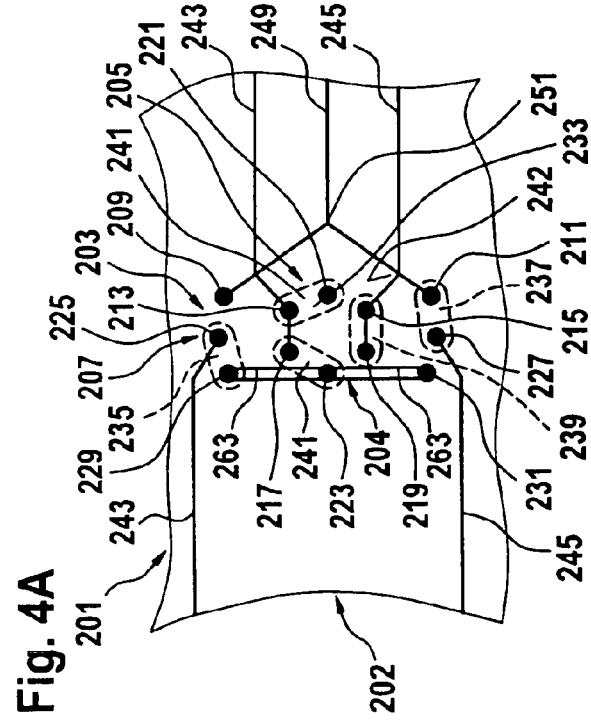

MICROLUIDIC VALVE HAVING TWO REVOLVING VALVE ELEMENTS

BACKGROUND ART

The present invention relates generally to microfluidic laboratory technology for chemical, physical, and/or biological analysis, separation, or synthesis of substances on a substrate with a microfluidic structure. It relates in particular to valves associated with microfluidic assemblies, and more specifically, to component parts of valves adapted to control the flow of liquid samples for analytical purposes.

There is a growing demand for biological fluid processing systems that have generated a need for small fluidic valves. Such miniaturized microfluidic devices has to fulfill a variety of requirements such as low dead volume and short flow paths with a cross section as constant as possible. This results generally in an improved performance characteristic. A sufficient approach in the field—compared for example to the use of valves with threaded connections—is the use of microfluidic chips coupled to revolving valve elements for flow controlling the microfluidic processes executed within the chip. One solution to reduce dead volumes is disclosed for example in the US 2003/0015682 A1. Due to enormous amounts of samples and components to be analyzed, efforts in the field are made as well to reduce analyzing time. These efforts have led to parallelized and more time efficient processes as shown for example in the EP 1 162 464 A1 or in the WO 01/84143 A1, but also to higher complexity of systems and executed processes, and consequently to an increased expenditure for controlling. In particular, coupling and flow controlling is an important matter of the latest developments in the technical field of microfluidic devices as shown for example in the EP 0 310 4413.4 (not published yet). Increasing the complexity of the processes executed by the microfluidic devices generally results disadvantageously in a higher amount of interconnections to be realized, switched, and/or flow controlled. HPLC valves are described in U.S. Pat. No. 5,616,300. Microfluidic valves are known from US2003/0015682 and US2003/0116206.

DISCLOSURE OF THE INVENTION

It is an object of the invention to provide an improved controlling, in particular flow controlling, of microfluidic devices. The object is solved by the independent claims. Preferred embodiments are shown by the dependent claims.

According to the present invention, the objects indicated are achieved by a component part of a microfluidic valve adapted to be coupled with a microfluidic device. The component part comprises a first revolving valve element with a first interface with the microfluidic device. The microfluidic device comprises at least one port. The component part is characterized by a second valve element with a second interface with the microfluidic device. The second revolving valve element is located within a through hole or recess of the first revolving valve element. A through hole is understood in this application as any kind of hole, bore, or opening having any shape. Embodiments may include one or more of the following. The port of the microfluidic device can be flow controlled by the interface. Liquid flowing through the port can be sealed or coupled to the flow path of the microfluidic device. Each valve element can flow-control the port or further ports of the microfluidic device. To couple, for example a first port flow-controlled by the first revolving valve element with a second port flow-controlled by the second revolving valve element, only a distance shorter than the diameter of the first revolving valve element has to be bridged by a flow path. This guarantees microfluidic devices with higher integrated microfluidic structures with minimal dead volume and consequently improved performance characteristics.

According to embodiments of the present invention, the valve elements are coaxially rotatable. Ports to be flow-controlled by the valve elements can be arranged in two concentric circles on the microfluidic device. An outer circle can be assigned to the first revolving valve element and an inner one to the second revolving valve element.

Embodiments may also include one or more of the following. Preferred the through hole is a cylindrical hole. The second revolving valve element has at least partly a cylindrical shape and is located within the first revolving valve element with a clearance fit. The clearance fit is easy to produce and behaves like a bearing for the second revolving valve element. The second revolving valve element can therefore be shaped like a shaft. Preferred the first revolving valve element has at least partly the shape of a hollow cylinder. Hollow cylinders can be produced easily, for example by turning and drilling.

Embodiments may also include one or more of the following. At least one of the valve elements has a coupling, in particular a step, for coupling with an actuator. With this, the valve elements can be easily adjusted. Preferred the valve elements are adapted to be actuated by rotating them coaxially, separately, or concurrently in any direction of rotating. Advantageously a variety of settings of the valve elements can be achieved. The second revolving valve element comprises a center blind hole or a through bore. The through bore can be connected to another flow path. The interfaces are adapted to interact with the port of the microfluidic device to flow-control and/or seal them. For this purpose, the interfaces of the valve elements comprise at least one fluid-conducting feature, for example a groove. The groove is preferred scratched, grinded, formed, or such in a substantially planar contact surface of the valve elements. The planar surface can be put against a surface of the microfluidic device for sealing the port.

The invention further relates to an assembly for handling liquid with a multi-route switching valve. The assembly comprises a microfluidic device, in particular a microfluidic chip. The valve can interact with the microfluidic device for flow-controlling the port. The assembly is characterized in that the valve is realized by the microfluidic device and a component part in any design as described above. Embodiments may include one or more of the following. The port is coupled to a flow path of the microfluidic device. The component part comprises at least two valve elements. The planar surface of the valve elements can be put against a surface of the microfluidic device close to the port for flow-controlling the port. A plurality of ports can be sealed, switched, or coupled by the valve to realize complex microfluidic processes to be executed with the device.

Embodiments may also include one or more of the following. The interfaces with the fluid-conducting features, the valve elements, and the microfluidic device realize the valve. The microfluidic device can be a disposable part, for example a cheaply producible microfluidic plastic chip. The valve elements that have to be highly dimensionally accurate, can be put or rather pressed against many different chips or more precise against a surface of the chips for coupling close to the ports of the chips. Preferred the microfluidic device is adapted for analyzing and/or separating components of a liquid, in particular by a detection area within or nearby the microfluidic flow path. This process can be easily controlled by the valve of the assembly.

BRIEF DESCRIPTION OF DRAWINGS

Other objects and many of the attendant advantages of embodiments of the present invention will be readily appreciated and become better understood by reference to the following more detailed description of preferred embodiments in connection with the accompanied drawings. Features that are substantially or functionally equal or similar will be referred to with the same reference signs.

FIG. 3 shows a schematic layout of a microfluidic chip with microfluidic structures, in particular flow paths and combination columns;

FIGS. 4A and 4B show detailed views of the microfluidic chip as shown in FIG. 3 together with a sketched component part of a microfluidic valve in two different settings;

DETAILED DESCRIPTION OF THE EMBODIMENTS

Figure 1:
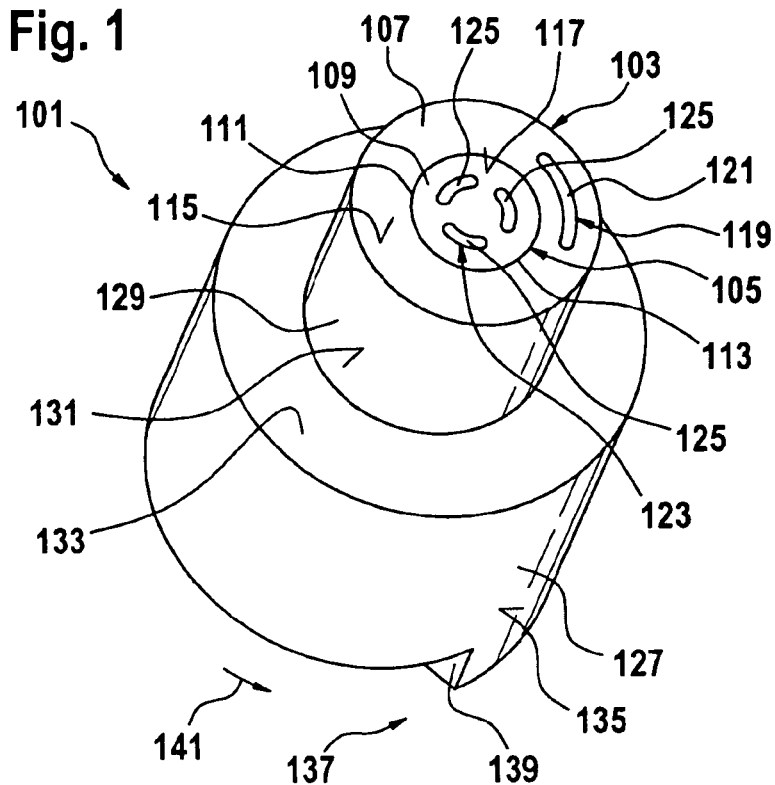
FIG. 1 shows a three-dimensional view of a component part of a microfluidic valve.

FIG. 1 shows a component part 101 of a microfluidic valve with a first revolving valve element 103 and a second revolving valve element 105. The valve elements 103 and 105 have a first interface 107 and a second interface 109 that can be coupled to a microfluidic device (not shown).

The second revolving valve element 105 is located in this embodiment within a cylindrical hole 111 of the first revolving valve element 103. Preferred the first revolving valve element 103 can comprise any kind of through hole instead of the cylindrical hole 111. In another preferred embodiment the through hole and accordingly the second revolving valve element 105 are conically formed.

Consequently, the second revolving valve element 105 can have at least partly the shape of a cone, fitting into the conical through hole of the first revolving valve element 103.

The second revolving valve element 105 has in this embodiment at least partly a cylindrical shape or rather the shape of a shaft. The second revolving valve element 105 and the cylindrical hole 111 of the first revolving valve element 103 build a clearance fit 113. The clearance fit 113 has the function of a bearing for the second revolving valve element 105.

The Interfaces 107 and 109 each comprise a substantially planar contact surface 115 and 117. The surface 115 of the first revolving valve element 103 comprises a first fluid conducting feature 119 comprising a first groove 121. The surface 117 of the second revolving valve element 105 comprises three further fluid conducting features 123 comprising three further grooves 125. The groves 121 and 125 are arranged along sectors of around 60° of concentric circles around the axis of rotation of the first revolving valve element 103 and the second revolving valve element 105. The elements 103 and 105 are coaxially rotatable by their center axis. The surfaces 115 and 117 each are rectangular to the center axis of the elements 103 and 105.

The first revolving valve element 103 comprises a body 127 with a greater diameter than the diameter of the first interface 107. The first revolving valve element 103 has partly the shape of a hollow cylinder 129 with a cylindrical surface 131. The diameter of the cylinder 129 widens at a circumferential step 133 of the first revolving valve element 103. The body also has the shape of a hollow cylinder with a cylindrical surface 135, but with a greater wall thickness than the hollow cylinder 129. The body 127 of the first revolving valve element 103 makes handling and coupling of the component part 101 easier.

The body 127 of the first revolving valve element 103 and the second revolving valve element 105 comprise a coupling 137 for coupling with an actuator (not shown). The coupling comprises in this embodiment a step 139 of the body 127 of the first revolving valve element 103. The step 139 can be engaged with an according lug or projection of the actuator. The actuator can apply a torque for rotating to the first revolving valve element 103 in at least one rotating direction—symbolized with an arrow 141. The first revolving valve element 103 can comprise a second step for rotating the first revolving valve element 103 in the opposite direction of rotation. The second revolving valve element 105 can comprise in embodiments according features to be rotated. The coupling 137 can comprise any other features for coupling like groves, flutes, and threads or alike. The elements 103 and 105 can be rotated synchronously or asynchronously in only one or any direction of rotation. For example, the second revolving valve element 105 can be adjusted in rotations by 60° in just one direction from a first setting to a second setting and back, because the grooves each are arranged rotationally symmetric in the surface 117 of the second revolving valve element 105. Consequently, the same setting results from a rotation of 120° of the grooves.

Figure 2:
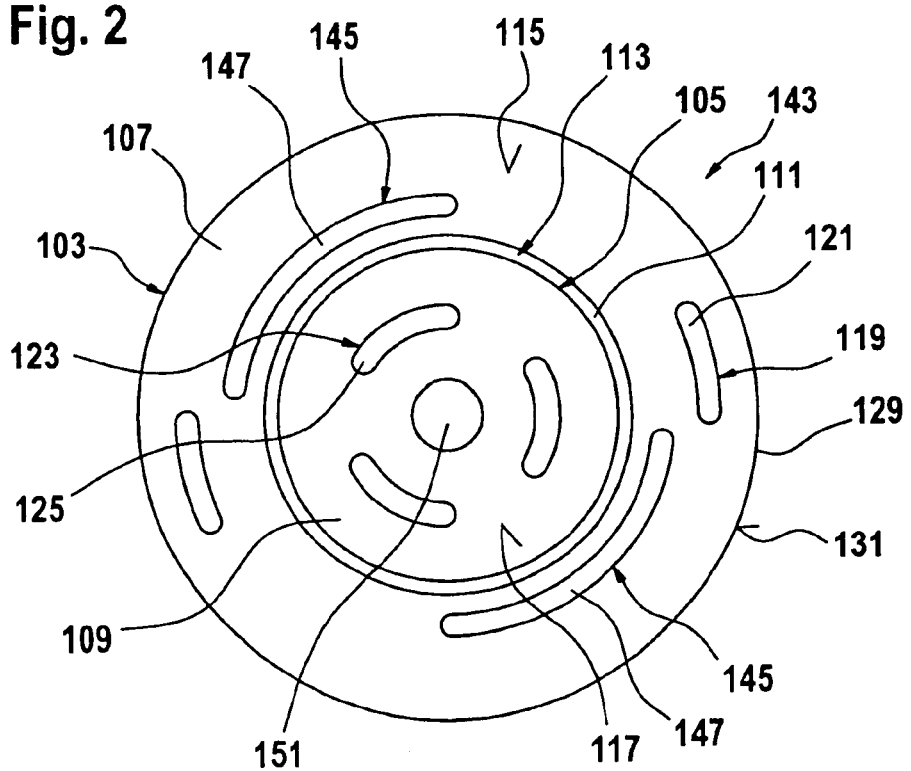
FIG. 2 shows a front view of an interface of another component part of a microfluidic valve.

FIG. 2 shows a front view of another component part 143 similar to the component part 101 of a microfluidic valve. Therefore, only the differences are described.

The second revolving valve element 105 of the component part 143 comprises two additionally fluid conducting features 145 with grooves 147. The grooves 147 are circular. The groves 147 and 121 are inserted 180° rotationally symmetric and in circles with different diameters in the surface 115 of the second revolving valve element 105. Consequently, the same setting results from a rotation of 180° of the grooves.

Ports of the microfluidic device can be arranged in three different circles. Ports arranged in a first circle can be flow-controlled by the grooves 125 of the second valve element 105, in a second circle by the grooves 147 of the first valve element 103, and in a third circle by the grooves 121 of the first valve element 103. By this, highly integrated and complex fluidic circuits with many interconnections to be controlled can be realized.

The second revolving valve element 105 of the component part 143 comprises a center blind hole 151 to avoid wearing and undefined condition of the surface 117 and any leaks.

The lengths of the grooves 125 of the second revolving valve element 105 are equal to the lengths of the grooves 121 of the first revolving valve element 103. Because of the different diameters of the valve elements 103 and 105, they have to be rotated in different angels for adjusting the grooves 121 and 125. Ports according to the groove 121 of the first revolving valve element 103 can be arranged relatively close to each other by this. Advantageously this results in short flow paths and low dead volumes. The rotational angel to adjust the grooves 121 and 125 of the valve elements 103 and 105 can be each adapted to the length of the grooves 121 and 125 separately by rotating the valve elements 103 and 105 independently.

FIG. 3 shows a schematic layout of a microfluidic chip 201 showing microfluidic structures, in particular flow paths and analytical columns, being part of a microfluidic assembly 202 for handling liquid with a multi-route switching valve 204.

The microfluidic chip 201 can comprise or consist of any material, preferred a flexible material, for example plastic or rather any polymeric material. In another preferred embodiment, the microfluidic chip 201 comprises polyimide.

FIGS. 4A and 4B show detailed views of the microfluidic chip 201 as shown in FIG. 3 together with a component part 203 of the microfluidic valve 204 in two different settings. The component part 203 comprises a first valve element 207 and a second valve element 205—each symbolized by dotted lines—realizing the multi-route switching valve 204 together with the microfluidic chip 201. The elements 205 and 207 are adapted for sealing and/or coupling one or more ports—12 ports 209 to 231 in this embodiment—of the microfluidic chip 201.

The FIGS. 3, 4A, and 4B show how highly integrated and parallelized processes that can be executed with the assembly 202 for handling liquid with a multi-route switching valve 204.

Figure 5A:
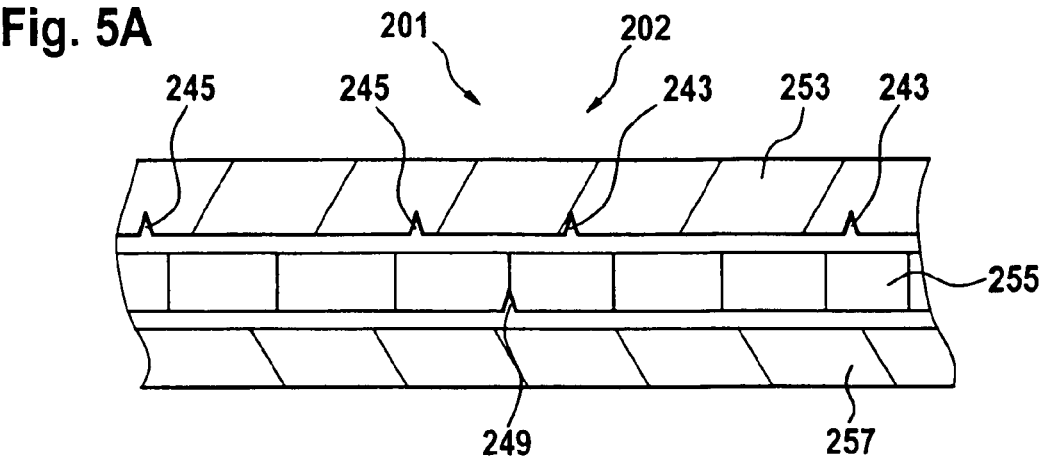
FIGS. 5A, 5B, and 5C show different cross-sectional views of the device of FIG. 3, taken along the lines A—A, B—B and C—C of FIG. 3.
Figure 5B:
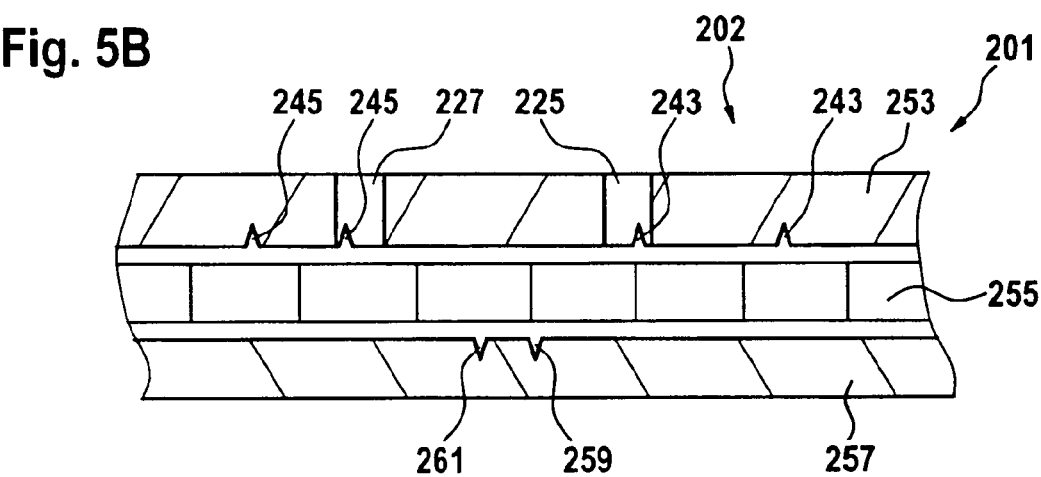
Figure 5C:
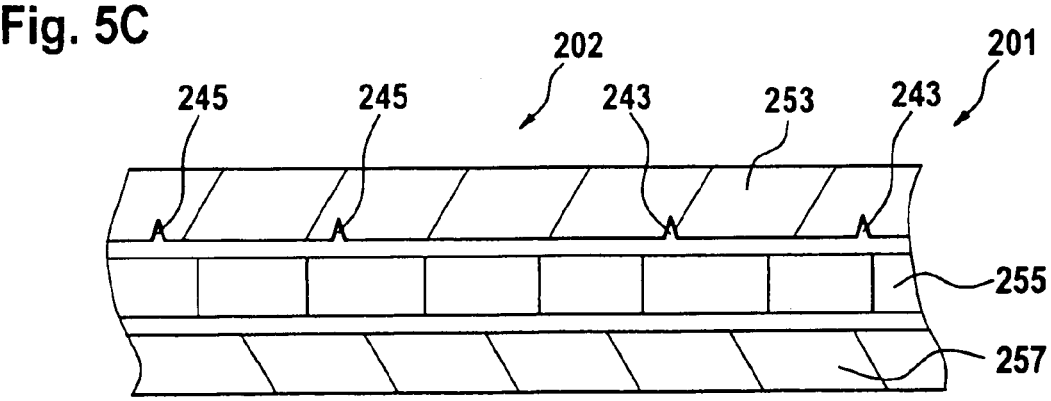

FIGS. 5A, 5B, and 5C show different cross-sectional views of the device of FIG. 3, taken along the lines A—A, B—B and C—C of FIG. 3.

Figure 6:
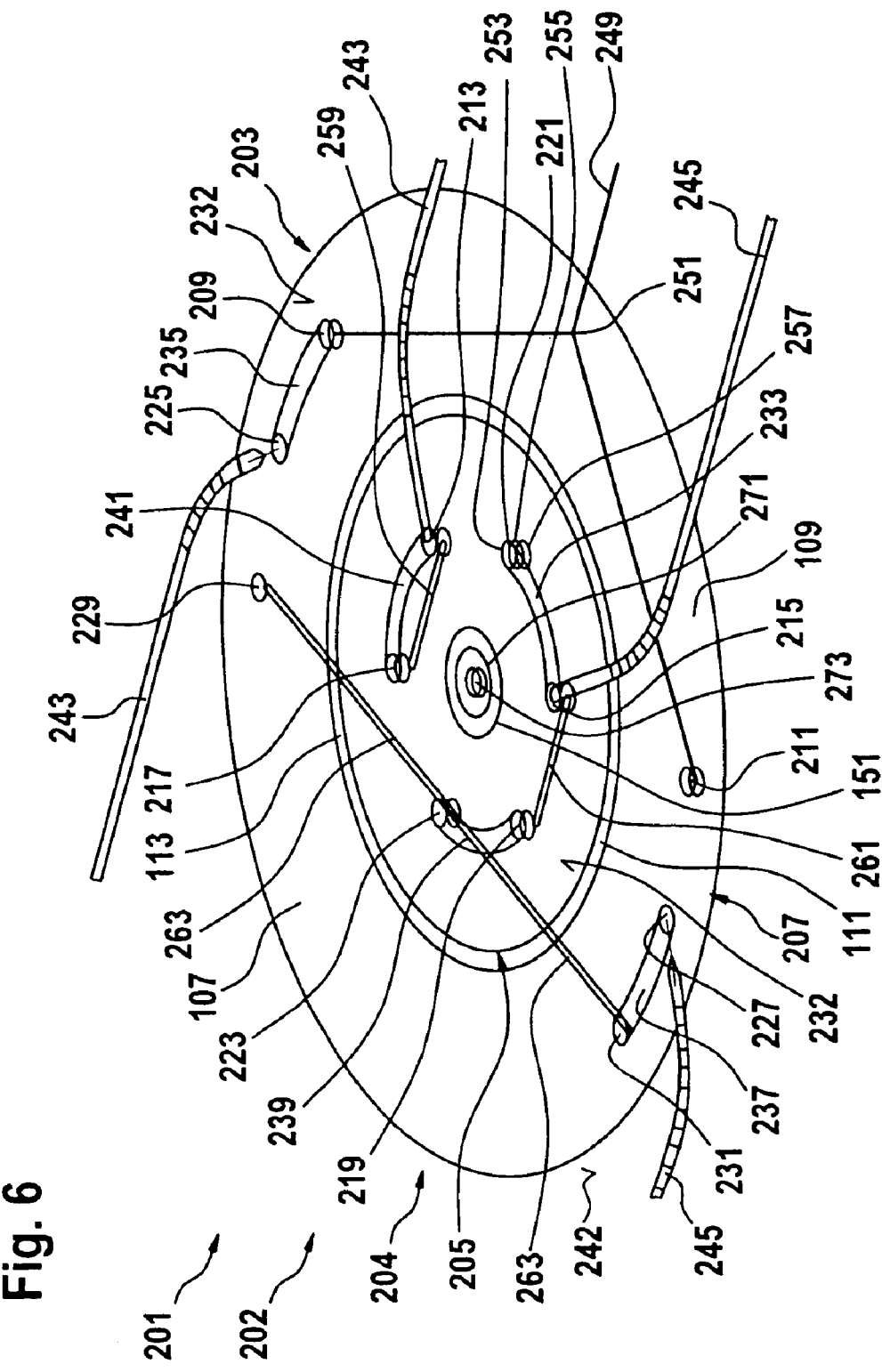
FIG. 6 shows a three-dimensional schematic view of another component part with a partially shown three-dimensional layout of the microfluidic chip of figure 3.

FIG. 6 shows a three-dimensional schematic view of the component part 203 and with the partially shown three-dimensional layout of the microfluidic chip 201 of the FIGS. 3 to 5.

The elements 205 and 207 have essentially a cylindrical shape, wherein the first valve element 207 has essentially the shape of a hollow cylinder. The second valve element 205 is arranged within the opening of the hollow cylinder of the first valve element 207. The concentric elements 205 and 207 are adapted to be rotated separately. Each of the elements 205 and 207 comprise an interface with a substantially planar surface 232 with at least one fluid-conducting feature, for example, a groove 233 to 241, to flow-control the ports of the microfluidic chip 201. Each interface comprises at least one of the groves 233 to 241—symbolized with dotted lines in the FIGS. 4A and 4B—to couple and/or to control the flux within the ports 209 to 231 of the microfluidic chip 201. The microfluidic chip 201 comprises a surface 242 for coupling with the substantially planar contact surfaces 232 of the interfaces of the valve elements close to the port.

The elements 205 and 207 can be adjusted by rotating them along their cylindrical middle axis. The ports 209 to 231 of the microfluidic chip 201 are arranged on circles or rather on the corner points of an equilateral hexagon—ports 213 to 223—in this embodiment.

The microfluidic chip 201 comprises a first combination column 243, a second combination column 245, a spray tip 247 and a flow path 249 coupled to the spray tip 247. The flow path 249 comprises a forking 251 coupled to a first analysis port 209 and a second analysis port 211.

By referring to the FIGS. 3 to 6 the layout of the microfluidic chip 201 and the processes executable with the microfluidic chip 201 are described as follows.

The microfluidic chip 201 comprises three layers, a top layer 253, a middle layer 255, and a bottom layer 257.

The top layer 253 comprises the combination columns 243 and 245. The middle layer 255 comprises the flow path 249 as shown in FIG. 5B with the forking 251. The bottom layer 257 comprises two flow paths 259 and 261 each coupled to an inlet port 213 or rather 215 and an outlet port 217 or rather 219 of the microfluidic chip 201. The inlet ports 213 and 215 are double ports each with two openings on the top side and on the bottom side of the microfluidic chip 201. The two openings are separated by the middle layer 255 of the microfluidic chip 201. The outlet ports 217 and 219 are located on the top side of the microfluidic chip 201 an can be realized by holes in the middle layer 255 and the top layer 253 of the microfluidic chip 201.

The inlet ports 213 and 215 can be coupled at the bottom side of the microfluidic chip 201 to two nano-pumps. Inflowing liquid can flow from the bottom side of the microfluidic chip 201 through the flow paths 259 and 261 in the bottom layer of the microfluidic chip 201, to the outlet ports 217 and 219 on the top side of the microfluidic chip 201.

The flow path 249 is implemented in the middle layer 255. The first combination column 243 and the second combination column 245 are implemented in the top layer 253. The first combination column 243 and the second combination column 245 cross the forking 251 of the flow path 249. This is possible because the middle layer 255 separates these flow paths.

In the following, the flow paths in a first setting of the elements 205 and 207 are described exemplarily by referring to the FIG. 4A. Ports, which are connected in the drawing with dotted lines, are coupled via the groves 233 to 241 in this first setting:

The first combination column 243 can be coupled upstream to a microfluidic sample-feeding device (not shown) via a sample inlet port 221 via a groove 233 of the second valve element 205, and via the inlet port 213. The sample inlet port 221 can be realized by a hole through all layers 253, 255, and 257 of the microfluidic chip 201. The sample inlet port 221 can be coupled at the bottom side of the microfluidic chip 201 to the sample-feeding device. The first combination column 243 can be coupled downstream to a waste container via a first column port 225, via a second outer groove 235 of the first valve element 207, via a first waste port 229, via a waste flow path 263, and via a waste outlet port 223 at the bottom side of the microfluidic chip 201. The waste flow path 263 is implemented in the middle layer 255 of the microfluidic chip 201 and is coupled to the waste outlet port 223. The waste container can be coupled at the bottom side of the microfluidic chip 201 or rather to the waste outlet port 223. The waste outlet port 223 can be realized by a hole through all layers 253, 255, and 257 of the microfluidic chip 201.

The flow path described above can be used for injecting a sample to the first combination column 243.

The second combination column 245 can be coupled upstream for example to a nano-pump via a the second inlet port 215 at the top side of the microfluidic chip 201, via a inner grove 239 of the second valve element 205, via the second outlet port 219, via the flow path 261, and via the second inlet port 215 at the bottom side of the microfluidic chip 201. The second combination column 245 can be coupled downstream to a laboratory apparatus (not shown) via a second column port 227, via a second outer groove 237 of the first valve element 207, via a second analysis port 211, via the forking 251 of the flow path 249, via the flow path 249, and via the spray tip 247 of the microfluidic chip 201.

Flow paths and processes resulting from the setting of the valve elements 205 and 207 as shown in FIG. 4B behave vice versa.

The flow path described above can be used for analyzing a liquid with a combination column as known in the art.

The microfluidic chip 201 is adapted to execute two processes in parallel.

The elements 205 and 207 can be adapted to interact with more or less than six ports. The layout of the microfluidic chip 201 can for example be transformed to interact with one six-port and one ten-port multi-route switching valve.

In another preferred embodiment the microfluidic chip 201 can have a detection area 269, for example an optical detection area, to analyze the liquid within the microfluidic chip 201, for example within the flow path 249.

In another preferred embodiment, the second valve element comprises, instead of or additionally to the center blind hole 151, a through bore 271—illustrated with dotted lines—and the microfluidic chip 201 comprises a center port 273. The port 273 can be fed alternatively or synchronously with liquid through the through bore 271 or can be connected to a waste container for realizing other microfluidic circuits.

In a further preferred embodiment, the microfluidic chip 201 comprises at least one hole 275 to align the microfluidic chip 201, in particular the ports of the microfluidic chip 201, relatively to the component part 203. In FIG. 3 the microfluidic chip 201 comprises two holes 275. The microfluidic chip 201 can be fitted to two pins (not shown) by the holes 275 to align the microfluidic chip 201. The component part 203 may be free to rotate but is positioned in a constant position to the pins.

In a further preferred embodiment, the second revolving valve element is located within and/or adjacent to a recess—instead of the through hole as described above—of the first revolving valve element. The first revolving valve element may have for example the shape of a half-hollow cylinder. In this example, the half-round inside of the half-hollow cylinder realizes the recess. The recess may have any other shape.

Finally, in preferred embodiments the component part 203 comprises more than two valve elements free to rotate to each other. Besides this, the microfluidic assembly can comprise more than one valve comprising a component part 203.

The invention claimed is:

1. Component part of a microfluidic valve adapted to be coupled with a microfluidic device, the microfluidic device having at least one port coupled to a flow path of the microfluidic device, the component part comprising a first revolving valve element having a first interface with the microfluidic device, and a second revolving valve element having a second interface with the microfluidic device and being located within a through hole or recess of the first revolving valve element.

2. The component part of claim 1, wherein at least one of the valve elements comprise at least one of the following features:
   a coupling, in particular a step, for coupling with an actuator,
   a center hole,
   a through bore,
   at least one fluid-conducting feature, in particular being inserted in the interfaces of the valve elements,
   at least one groove, in particular being part of the fluid-conducting feature,
   at least one substantially planar contact surface, in particular being part of the interfaces of the valve elements.

3. The component part of claim 1, wherein the through hole is a cylindrical hole, and wherein the second revolving valve element has at least partly a cylindrical shape and is located within the first revolving valve element by a clearance fit, wherein in particular the first revolving valve element has at least partly the shape of a hollow cylinder.

4. The component part of claim 1, wherein the valve elements are rotatable coaxially, in particular are adapted to be actuated by rotating them coaxially by the actuator separately or concurrently in any direction of rotating.

5. The component part of claim 1, wherein the interfaces of the valve elements are adapted to interact with the port, in particular with 12 ports, of the microfluidic device.

6. An assembly for handling liquid with a multi-route switching valve comprising a microfluidic device, in particular a microfluidic chip, wherein the microfluidic device is adapted for interacting with the valve and comprises at least one port, wherein the port is flow controlled by the valve, in particular sealed, switched, or coupled, wherein the microfluidic device comprises at least one microfluidic flow path coupled to the port, wherein the valve is realized by the microfluidic device and a component part according to claim 1.

7. The assembly of claim 6, wherein the valve is realized by the interfaces, by the fluid-conducting features of the interfaces of the valve elements, and by the microfluidic device.

8. The assembly of claim 6, wherein the microfluidic device comprises a surface for coupling with the substantially planar contact surface/s of the interfaces of the valve elements close to the port.

9. The assembly of claim 6, wherein the microfluidic device is adapted for analyzing and/or separating components of a liquid, in particular by a detection area within or close to the microfluidic flow path.

10. The assembly of claim 6, wherein the first combination column and the second combination column cross the flow path, in particular a forking of the flow path.

* * * * *

UNITED STATES PATENT AND TRADEMARK OFFICE
CERTIFICATE OF CORRECTION

| | |
|---|---|
| PATENT NO. | : 7,143,787 B1 |
| APPLICATION NO. | : 11/134131 |
| DATED | : December 5, 2006 |
| INVENTOR(S) | : Bauerle et al. |

It is certified that error appears in the above-identified patent and that said Letters Patent is hereby corrected as shown below:

In Column 8, line 46, claim 8, delete "sufaces/s" and insert -- surfaces --, therefor.

Signed and Sealed this

Twentieth Day of February, 2007

JON W. DUDAS
*Director of the United States Patent and Trademark Office*